US008946137B2

(12) United States Patent
Kimura et al.

(10) Patent No.: US 8,946,137 B2
(45) Date of Patent: Feb. 3, 2015

(54) FOAMABLE SKIN WASHING AGENT

(71) Applicant: Shiseido Company, Ltd., Tokyo (JP)

(72) Inventors: Tomohiko Kimura, Yokohama (JP); Hidefumi Araki, Yokohama (JP)

(73) Assignee: Shiseido Company, Ltd., Tokyo (JP)

(*) Notice: Subject to any disclaimer, the term of this patent is extended or adjusted under 35 U.S.C. 154(b) by 0 days.

(21) Appl. No.: 13/705,517

(22) Filed: Dec. 5, 2012

(65) Prior Publication Data

US 2013/0178406 A1 Jul. 11, 2013

Related U.S. Application Data

(63) Continuation of application No. 12/935,311, filed as application No. PCT/JP2009/056375 on Mar. 27, 2009, now abandoned.

(30) Foreign Application Priority Data

Mar. 31, 2008 (JP) ................ 2008-089209

(51) Int. Cl.
*A61K 8/39* (2006.01)
*A61K 8/81* (2006.01)
*A61Q 19/10* (2006.01)
*A61K 8/42* (2006.01)
*C11D 1/835* (2006.01)
*C11D 1/72* (2006.01)
*C11D 1/62* (2006.01)

(52) U.S. Cl.
CPC . *A61K 8/39* (2013.01); *A61K 8/817* (2013.01); *A61Q 19/10* (2013.01); *C11D 1/72* (2013.01); *A61K 8/42* (2013.01); *C11D 1/835* (2013.01); *C11D 1/62* (2013.01); *A61K 8/8158* (2013.01)
USPC ............ 510/130; 510/152; 510/475; 510/499

(58) Field of Classification Search
None
See application file for complete search history.

(56) References Cited

U.S. PATENT DOCUMENTS

2009/0010867 A1  1/2009  Kimura et al.

FOREIGN PATENT DOCUMENTS

| JP | 62-4799 | 1/1987 |
|---|---|---|
| JP | 62-18500 | 1/1987 |
| JP | 2001-64678 | 3/2001 |
| JP | 2003-73257 | 3/2003 |
| JP | 2004-35524 | 2/2004 |
| JP | 2005-298455 | 10/2005 |
| JP | 2006-282894 | 10/2006 |
| JP | 2006-282895 | 10/2006 |
| JP | 2007-146029 | 6/2007 |
| JP | 2008-231346 | 10/2008 |
| WO | 2006/087939 A1 | 8/2006 |
| WO | 2006/137511 | 12/2006 |

OTHER PUBLICATIONS

International Search Report for corresponding PCT/JP2009/056375 mailed Jun. 23, 2009, three pages.
Nozaki "Research and development of body cleanser," Fragrance Journal, 1996, seven pages.
English translation of the excerpt of Nozaki "Research and development of body cleanser," p. 27, right column, lines 9-3 from the bottom, one page.
Partial English translation of JP Publication No. 2001-064678 published Mar. 13, 2001, five pages.
Partial English translation of JP Publication No. 2003-073257 published Mar. 12, 2003, six pages.
Partial English translation of JP Publication No. 2004-035524 published Feb. 5, 2004, 15 pages.
Partial English translation of JP Publication No. 2006-282894 published Oct. 19, 2006, 11 pages.
Partial English translation of JP Publication No. 2006-282895 published Oct. 19, 2006, seven pages.
Partial English translation of JP Publication No. 2007-146029 published Jun. 14, 2007, 13 pages.

*Primary Examiner* — Necholus Ogden, Jr.
(74) *Attorney, Agent, or Firm* — Rankin, Hill & Clark LLP

(57) ABSTRACT

To provide a skin washing agent which is excellent in the foaming speed and the foam creaminess in washing therewith, and which, after washing therewith, is excellent in the moist feeling and the absence of pulling feeling of the skin and does not change the moisture content of skin. A foamable skin washing agent comprising (a) a fatty acid salt, (b) one or more selected from a homopolymer, a dipolymer and a terpolymer derived from a specific cationated monomer (e.g., dimethyldiallylammonium chloride), (c) a polyglyceryl monoalkyl ether, and (d) one or more selected from an acylmethyltaurine salt and a hydroxy ether carboxylate salt.

4 Claims, No Drawings

FOAMABLE SKIN WASHING AGENT

TECHNICAL FIELD

The present invention relates to a foamable skin washing agent which has sufficient detergency to the dirt of a skin surface, and is especially excellent in the foaming speed and the foam creaminess in washing therewith, and which ameliorates a pulling feeling of the skin after washing therewith, and improves a moist feeling and does not lower the moisture content of the skin.

BACKGROUND ART

Of skin washing agents, the properties of the foams to form in washing therewith and the feeling in use thereof are important points to be preferred by consumers, in addition to the primary function of detergency thereof. In particular, those capable of foaming rapidly, capable of forming fine and creamy foams and capable of giving a moist feeling to skin without dehydrating it after washing therewith not giving any skin pulling feeling tend to be preferred by consumers.

Regarding the problems, various types of surfactants, oily ingredients, polymers or the like are heretofore broadly incorporated in the base of a skin washing agent to thereby favorably improve the feeling of foams and the feeling of skin. However, a skin washing agent with a surfactant having high detergency incorporated therein has some problems in that it roughens skin excessively and, after toweling, it may often give a skin-tightness or skin pulling feeling. In addition, it has another problem in that the moisture may be removed from the skin washed therewith and the moisture content of the skin may be thereby reduced.

As a technique of incorporating a surfactant in the base of a skin washing agent, for example, there is proposed a method of incorporating a polyglycerin monoalkyl ether therein (e.g., see Patent References 1 and 2). However, incorporation of such a polyglycerin monoalkyl ether lowers the elasticity of foams, and is therefore unsatisfactory to users since they could not have a feeling of creamy foams.

Additionally, a washing agent is proposed which comprises a combination of a polyglycerin monoalkyl ether, a fatty acid salt, and an ampholytic surfactant and/or a semipolar surfactant (see Patent Reference 3). The combination could give a refreshed feeling but may give a pulling feeling of the skin, and is insufficient in point of the foaming speed and the quality of foams and is therefore unsatisfactory to users.

On the other hand, as a technique of enhancing the foamability and the quality of foams, there is proposed a method of incorporating a polymer in the base of a skin washing agent. For example, there are known a skin washing agent with a polydimethyldiallylammonium chloride or a dimethyldiallylammonium chloride/acrylamide copolymer incorporated therein (e.g., see Patent Reference 4), a skin washing agent with an acrylic acid/dimethyldiallylammonium chloride/acrylamide terpolymer incorporated therein (e.g., see Patent References 5 and 6).

However, these skin washing agents with such a polymer incorporated therein could not be said still satisfactory in point of the foaming speed, and it is difficult to say that the agents could attain a sufficient effect in point of giving a moist feeling with no pulling feeling of the skin washed with them.

Patent Reference 1: JP 2006-282894A
Patent Reference 2: JP 2006-282895A
Patent Reference 3: JP 2007-146029A
Patent Reference 4: JP 62-4799A
Patent Reference 5: JP 2001-64678A
Patent Reference 6: JP 2003-73257A

DISCLOSURE OF THE INVENTION

Problems that the Invention is to Solve

In consideration of the above-mentioned prior-art problems, an object of the present invention is to provide a skin washing agent which is excellent in the foaming speed and the foam creaminess in washing therewith, and which, after washing therewith, is excellent in a moist feeling and being free from pulling feeling of the skin, and which does not lower the moisture content of the skin.

Means for Solving the Problems

Heretofore, soap (fatty acid alkali salt) has been used as the main ingredient of a skin washing agent because of its detergency. However, soap bonds with a divalent metal ion, such as calcium, magnesium or the like, in tap water to form a water-insoluble metal soap (scum), which is said to have some negative influences on the refreshed feeling and other good feelings peculiar to soap, and adhere to skin to give thereto a skin-pulling feeling or reduce the moisture content of skin. The method for preventing such scum from adhering to skin may be divided broadly into two, a method of preventing/controlling the formation of scum, and another method of making the formed scum readily removable by washing to thereby prevent the scum from adhering to skin. The former method of preventing/controlling the formation of scum includes use of non-soap washing agents, control of counter ions and the like, which, however, involve some problems in that the production cost is high and the usable base is limited. On the other hand, the latter method of making the formed scum readily removable by washing to thereby prevent the scum from adhering to skin includes use of some additive to enhance the scum dispersibility. This method may utilize the conventional soap technology for the washing agent therein and is therefore advantageous in point of the production cost in that it is free from limitation on the usable base.

Specifically, the present invention provides a foamable skin washing agent comprising (a) a fatty acid salt, (b) one or more polymers selected from a homopolymer, a dipolymer and a terpolymer derived from a cationated monomer represented by the following formula (I):

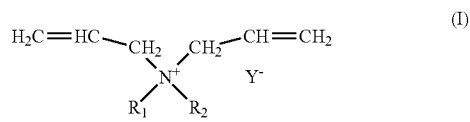

(in formula (I), $R_1$ and $R_2$ each independently represent a hydrogen atom, or an alkyl group having from 1 to 4 carbon atoms; and $Y^-$ represents a monovalent inorganic or organic anion), (c) a polyglyceryl monoalkyl ether represented by the following formula (II):

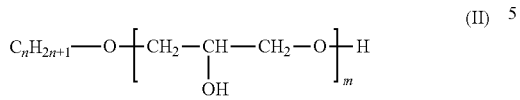

(in the formula (II), n indicates an integer of from 6 to 22, and m indicates an integer of 3 or more), (d) one or more selected from an acylmethyltaurine salt and a hydroxy ether carboxylate salt.

Preferably, component (b) is one or more polymers selected from dimethyldiallylammonium chloride polymers, dimethyldiallylammonium chloride/acrylamide copolymers, and dimethyldiallylammonium chloride/acrylamide/acrylic acid copolymers.

Advantage of the Invention

The foamable skin washing agent of the invention has the advantages of detergency, rapid foamability in washing, excellent creaminess of foams, impartation of no pulling feeling of the skin after washing, impartation of moist feeling to skin and no influence of reducing the skin moisture content, which are remarkably more excellent than those of conventional washing agents.

BEST MODE FOR CARRYING OUT THE INVENTION

The invention is described in detail hereinunder.

Component (a), fatty acid salt for use in the invention is a fatty acid soap and is preferably a fatty acid salt having from 10 to 22 carbon atoms. The salt includes alkali metal salts, organic amine salts, and ammonium salts. Specific examples of the component (a) include sodium laurate, sodium myristate, sodium palmitate, sodium stearate, sodium oleate, potassium laurate, potassium myristate, potassium palmitate, potassium stearate, and potassium oleate. These may be prepared, for example, by neutralizing the corresponding fatty acid with an alkali, such as potassium hydroxide, sodium hydroxide, triethanolamine or the like. One or more of those may be employed here as component (a).

The amount of component (a) to be in the skin washing agent of the invention may be within a range of from 2 to 90% by mass of the agent, but its preferred amount may differ depending on the formulation of the agent. In a liquid washing agent, the amount is preferably from 5 to 30% by mass, and in a creamy washing agent, the amount is preferably from 10 to 50% by mass. When the amount of component (a) is less than 2% by mass, then the foamability and the refreshed feeling would not be sufficient; but on the other hand, when more than 90% by mass, then the viscosity and the hardness of the base would increase and the producibility may worsen.

Component (b) is one or more polymers selected from a homopolymer, a dipolymer and a terpolymer derived from a cationated monomer represented by the following formula (I):

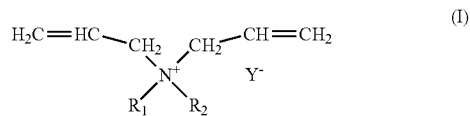

In formula (I), the definitions of the substituents are as follows:

$R_1$ and $R_2$ each independently represent a hydrogen atom, or an alkyl group having from 1 to 4 carbon atoms. The alkyl group may be linear or branched, and may be partly substituted with a hydroxyl group or a fluorine atom. The said substituted or unsubstituted alkyl group having from 1 to 4 carbon atoms includes a methyl group, an ethyl group, a propyl group, a butyl group, a 2-hydroxyethyl group, a 2-hydroxypropyl group, a trifluoromethyl group, and a trifluoroethyl group.

$Y^-$ represents a monovalent inorganic or organic anion. The monovalent inorganic anion includes a chloride ion, a fluoride ion, and an iodide ion; and the monovalent organic anion includes a sulfate ion, an acetate ion, a benzenesulfonate ion, and a phosphate ion.

Examples of the cationated monomer represented by the above formula (I) include dimethyldiallylammonium chloride, diethyldiallylammonium chloride, dipropyldiallylammonium chloride, dimethyldiallylammonium sulfate, diethyldiallylammonium sulfate, and dipropyldiallylammonium sulfate. Of those, preferred for use herein is dimethyldiallylammonium chloride (hereinafter this may be referred to as "DADMAC").

A polymer composed of only the cationated monomer of formula (I) is the homopolymer. A copolymer composed of the cationated monomer of formula (I) and any other monomer is the dipolymer or the terpolymer, the former comprising one other monomer but the latter comprising two other monomers.

Component (b) is broadly divided into categories of a cationated polymer and an ampholytic polymer depending on the monomer combination therein. The homopolymer is produced from only the cationated monomer of formula (I), and is therefore a cationated polymer. A copolymer of a cationated monomer and a nonionic monomer is categorized as a cationated polymer. On the other hand, a polymer produced through copolymerization of a cationated monomer and an anionic monomer or an ampholytic monomer is an ampholytic polymer.

The nonionic monomer copolymerizable with the cationated monomer of formula (I) is not specifically defined; and its preferred examples include acrylamide, methacrylamide, N-methylacrylamide, N-methylmethacrylamide, N,N-dimethylacrylamide, N,N-diethylmethacrylamide, N-cyclohexylacrylamide, N-cyclohexylmethacrylamide, N,N-di(ethylene glycol)acrylamide, N,N-di(ethylene glycol)methacrylamide, N-polyethylene glycol (10 mol) acrylamide, N-polyethylene glycol (10 mol) methacrylamide, N-polyethylene glycol ethyl ether (10 mol) acrylamide, and N-polyethylene glycol ethyl ether (10 mol) methacrylamide. Of those, more preferred is acrylamide.

The anionic monomer copolymerizable with the cationated monomer of formula (I) is not specifically defined; and its preferred examples include acrylic acid, methacrylic acid, sodium acrylate, sodium methacrylate, ammonium acrylate, and ammonium methacrylate. Of those, more preferred is acrylic acid.

The ampholytic monomer copolymerizable with the cationated monomer of formula (I) includes monomers having one or more betaine skeletons in the molecule (e.g., N-aminopropylacrylamide-betaine, N-aminopropylmethacrylamide-betaine), but not limited thereto.

The content of the cationated monomer of formula (I) in component (b) is preferably from 2 to 100% by mass of the amount of all the constitutive monomers, more preferably from 5 to 100% by mass. When the content is less than 2% by mass, then the nature of the other monomer to be copolymerized would be too strong and the present monomer could not fully exhibit its function. Preferably, the mass-average molecular weight of component (b) is from 5,000 to 7,500,000, more preferably from 10,000 to 5,000,000.

As component (b), a dimethyldiallylammonium (DADMAC) polymer is a preferred example of the homopolymer; a DADMAC/acrylamide copolymer is a preferred example of the dipolymer; and a DADMAC/acrylamide/acrylic acid copolymer is a preferred example of the terpolymer. However, the ingredient is not limited to these examples.

The constituent ratio (by mass) of the two monomers in the DADMAC/acrylamide copolymer is preferably from 10/90 to 90/10 as DADMAC/acrylamide, more preferably from 80/20 to 20/80.

The constituent ratio (by mass) of the three monomers in the DADMAC/acrylamide/acrylic acid copolymer is preferably from 40/20/40 to 10/80/10 as DADMAC/acrylamide/acrylic acid, more preferably from 25/50/25 to 20/60/20.

Component (b) may be produced through polymerization or copolymerization in any known polymerization method using the cationated monomer of formula (I) or using it along with any other copolymerizing monomer.

Commercial products may be used as component (b). For example, the DADMAC polymer is commercially available as "Merquat 100" (by Nalco Company), "ME Polymer H40W" (by Toho Chemical Industry Co., Ltd.). The DADMAC/acrylamide copolymer is commercially available as "Merquat 550" (by Nalco Company), "ME Polymer 09W" (by Toho Chemical Industry Co., Ltd.). The DADMAC/acrylamide/acrylic acid copolymer is commercially available as "Marcoat Plus 3300", "Marcoat Plus 3331". (both by Nalco), "ME Polymer T-343" (by Toho Chemical). These may be used favorably here. Needless-to-say, however, the ingredient is not limited to these examples.

Preferably, the amount of component (b) to be in the skin washing agent composition of the invention is from 0.01 to 10% by mass, more preferably from 0.05 to 5% by mass. When the amount is less than 0.01% by mass, then the creaminess of foams would be insufficient; but on the other hand, when more than 10% by mass, then the foaming speed may lower in some degree and the agent may give a slimy feeling in rinsing.

Component (c) for use in the invention is a polyglyceryl monoalkyl ether represented by the following formula (II), and this is a nonionic surfactant.

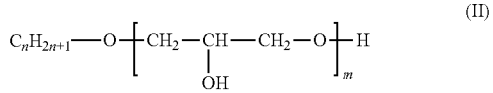

(II)

In the formula (II), n indicates an integer of from 6 to 22, and is preferably from 8 to 16. When n is more than 22, the foaming may be slow; but on the other hand, when less than 6, the creaminess of foams may tend to be poor.

m indicates an integer of 3 or more, and is preferably from 3 to 25, more preferably from 4 to 20, even more preferably from 4 to 10. When m is less than 3, or when the number of m is too large, then the effect of the ingredient to prevent the skin pulling feeling after washing would be poor.

In formula (II), the alkyl group ($C_nH_{2n+1}$) may be linear, branched or cyclic, and concretely includes a linear alkyl group, such as a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group; a branched alkyl group, such as a 2-ethylhexyl group, a 2-methylhexyl group, a 2-methylnonyl group, a 2-octyldecyl group, a 3,5,5-trimethylhexyl group, and an isostearyl group; a cyclic alkyl group such as a cyclohexyl group.

Component (c) is commercially available, for example, as "Sunether L-4" (=polyglyceryl-4 lauryl ether), "Sunether L-10" (both by Taiyo Chemical Industry Co., Ltd.), etc.; and these are favorably used here.

The amount of component (c) to be in the skin washing agent composition of the invention is preferably from 0.01 to 20% by mass, more preferably from 0.05 to 10% by mass, even more preferably from 0.1 to 5% by mass. When the amount is less than 0.01% by mass, then the ingredient would be ineffective for sufficient foaming and for ameliorating feeling effects; but on the other hand, when more than 20% by mass, the composition may be difficult to prepare and its feeling in use would be poor. One or more of the compounds may be used as component (c).

Component (d) in the invention is one or more selected from an acylmethyltaurine salt and a hydroxyalkyl ether carboxylate salt.

The acylmethyltaurine salt is an anionic surfactant represented by the following formula (III):

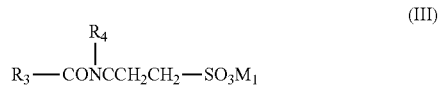

(III)

In formula (III), $R_3$ represents an alkyl group or an alkenyl group having from 7 to 21 carbon atoms; and $R_4$ represents an alkyl group having from 1 to 3 carbon atoms.

$M_1$ represents an alkali metal (e.g., lithium, potassium, sodium), an alkaline earth metal (e.g., calcium, magnesium), an ammonium or an organic amine (e.g., monoethanolamine, triethanolamine).

The acylmethyltaurine salt concretely includes N-lauroylmethyltaurine sodium, N-myristoylmethyltaurine sodium, N-palmitoylmethyltaurine sodium, and N-stearoylmethyltaurine sodium. Of those, preferred are N-lauroylmethyltaurine sodium and N-myristoylmethyltaurine sodium from the viewpoint of the foamability thereof. N-cocoylmethyltaurine sodium obtained from palm oil that is a vegetable oil is a mixture of the above-mentioned N-lauroylmethyltaurine sodium, N-myristoylmethyltaurine sodium and N-palmitoylmethyltaurine sodium, and is therefore preferred for use here.

The hydroxyalkyl ether carboxylate salt is an anionic surfactant represented by the following formula (IV):

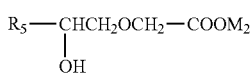

$$R_5-CHCH_2OCH_2-COOM_2$$
$$|$$
$$OH$$
(IV)

In formula (IV), $R_5$ represents an alkyl group having from 8 to 20 carbon atoms. $M_2$ represents an alkali metal (e.g., lithium, potassium, sodium), an alkaline earth metal (e.g., calcium, magnesium), an ammonium or an organic amine (e.g., monoethanolamine, triethanolamine).

Preferred examples of the hydroxyalkyl ether carboxylate salt include sodium dodecane-1,2-diol acetate ether, but not limited thereto.

The amount of component (d) to be in the skin washing agent composition of the invention is preferably from 1 to 20% by mass of the composition, more preferably from 2 to 10% by mass, even more preferably from 3 to 5% by mass. When the amount is less than 1% by mass, then the ingredient may be ineffective for rapid foamability and foam formation and the composition could not foam well and would be ineffective for ameliorating feeling effects; but on the other hand, when more than 20% by mass, then it is unfavorable since a lot of time may be taken for rinsing. One or more such compounds may be employed here as component (d).

The production method of the skin washing agent of the invention is not specifically defined. The agent may be produced in an ordinary manner. Briefly, for example, a fatty acid is added to water, and dissolved therein under heat at about 70° C. A potassium hydroxide solution is added thereto to neutralize it thereby preparing a soap solution (component (a)). Next, component (b), component (c) and component (d) are added to it and well stirred, and then rapidly cooled to about 25° C. to give a skin washing agent. However, the production method is not limited to this example.

The skin washing agent of the invention may contain any other ingredient that may be generally incorporated in ordinary washing agents, in addition to the above-mentioned components (a) to (d), within a range not detracting from the object and the effect of the washing agent of the invention. The additional ingredient includes surfactants (except the above-mentioned component (c) and component (d)). The type of the other surfactant that may be in the agent of the invention is not specifically defined, and any of anionic surfactants, cationic surfactants, ampholytic surfactants and nonionic surfactants may be in the agent.

The anionic surfactants include higher alkyl sulfate salts, such as sodium lauryl sulfate, sodium lauryl sulfate, and potassium lauryl sulfate; alkyl ether sulfate salts, such as POE-lauryl sulfate triethanolamine, and POE-sodium lauryl sulfate; N-acylsarcosine acids, such as sodium lauroylsarcosinate; phosphate salts, such as POE-oleyl ether sodium phosphate, and POE-stearyl ether phosphoric acid; sulfosuccinate salts, such as sodium di-2-ethylhexylsulfosuccinate, monolauroyl monoethanolamide polyoxyethylene sodium sulfosuccinate, and laurylpolypropylene glycol sodium sulfosuccinate; alkylbenzenesulfonate salts, such as sodium linear dodecylbenzenesulfonate, linear dodecylbenzenesulfonic acid triethanolamine, and linear dodecylbenzenesulfonic acid; higher fatty acid ester sulfate salts, such as hardened coconut oil fatty acid glycerin sodium sulfate; N-acylglutamate salts, such as monosodium N-lauroylglutamate, disodium N-stearoylglutamate, and monosodium N-myristoyl-L-glutamate; sulfate oils, such as Turkish red oil; POE-alkyl ether carboxylic acids; POE-alkylallyl ether carboxylate salts; α-olefinsulfonate salts; higher fatty acid ester sulfonate salts; dialcohol sulfate salts; higher fatty acid alkylamide sulfate salts; sodium lauroyl monoethanolamide succinate; N-palmitoylaspartic acid ditriethanolamine; and casein sodium.

The cationic surfactants include alkyltrimethylammonium salts, such as stearyltrimethylammonium chloride, and lauryltrimethylammonium chloride; alkylpyridinium salts, such as cetylpyridinium chloride; distearyldimethylammonium chloride dialkyldimethylammonium salts; poly(N,N'-dimethyl-3,5-methylenepiperidinium)chloride; alkyl quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzetonium chloride.

The ampholytic surfactants include imidazoline-type ampholytic surfactants, such as 2-undecyl-N,N,N-(hydroxyethylcarboxymethyl)-2-imidazoline sodium, and 2-cocoyl-2-imidazolinium hydroxide-1-carboxyethyloxy disodium salt; betaine-type surfactants, such as 2-heptadecyl-N-carboxymethyl-N-hydroxyethylimidazolinium betaine, lauryldimethylaminoacetate betaine, alkylbetaines, amidebetaines, and sulfobetaine.

The oleophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexyl; glycerin polyglycerin fatty acids, such as monocottonseed oil fatty acid glycerin, glycerin monoerucate, glycerin sesquioleate, glycerin monostearate, glycerin α,α'-oleate pyroglutamate, and glycerin monostearate malate; propylene glycol fatty acid esters, such as propylene glycol monostearate; hardened castor oil derivatives; and glycerin alkyl ethers.

The hydrophilic nonionic surfactants include POE-sorbitan fatty acid esters, such as POE-sorbitan monooleate, POE-sorbitan monostearate, POE-sorbitan monooleate, and POE-sorbitan tetraoleate; POE-sorbitol fatty acid esters, such as POE-sorbitol monolaurate, POE-sorbitol monooleate, POE-sorbitol pentaoleate, and POE-sorbitol monostearate; POE-glycerin fatty acid esters, such as POE-glycerin monostearate, POE-glycerin monoisostearate, and POE-glycerin triisostearate, etc., POE-monooleate; POE-fatty acid esters, such as POE-distearate, POE-monodioleate, and ethylene glycol distearate; POE-alkyl ethers, such as POE-lauryl ether, POE-oleyl ether, POE-stearyl ether, POE-behenyl ether, POE-2-octyldodecyl ether, and POE-cholestanol ether; Pulronic-type surfactants, such as Pulronic; POE/POP-alkyl ethers, such as POE/POP-cetyl ether, POE/POP-2-decyltetradecyl ether, POE/POP-monobutyl ether, POE/POP-hydrogenated lanolin, and POE/POP-glycerin ether; tetra-POE/tetra-POP-ethylenediamine condensates, such as Tetronic; POE-(hardened) castor oil derivatives, such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate; POE-beeswax/lanolin derivatives, such as POE-sorbitol beeswax; alkanolamides, such as cocoyldiethanolamide, lauroylmonoethanolamide, and fatty acid isopropanolamide; POE-propylene glycol fatty acid esters; POE-alkylamines; POE-fatty acid amides; sucrose fatty acid esters; alkylethoxydimethylamine oxides; and trioleyl phosphate.

The skin washing agent of the invention may contain any other ingredient that may be generally incorporated in ordinary cosmetics and medicines, in addition to the above-mentioned ingredients, within a range not detracting from the object and the effect of the invention. The additional ingredient includes moisturizers, powdery ingredients, liquid oils and fats, solid oils and fats, waxes, hydrocarbon oils, higher fatty acids, higher alcohols, synthetic ester oils, silicone oils, natural water-soluble polymers, semisynthetic water-soluble polymers, synthetic water-soluble polymers, tackifiers, UV absorbents, metal ion scavengers, lower alcohols, polyalcohols, monoses, oligosaccharides, polysaccharides, amino acids, organic amines, polymer emulsions, pH regulators, antioxidants, antioxidation promoters, preservatives, antiphlogistics, whitening agents, various extracts, activators, blood circulation promoters, antiseborrheics, and antiinflammatory agents.

Preferably in the invention, a moisturizer (e.g., polyalcohol such as glycerin, polyethylene glycol, propylene glycol, 1,3-butylene glycol, hexylene or the like) is incorporated in the washing agent preferably in an amount of from 10 to 40% by mass or so, more preferably in an amount of from 20 to 35% by mass, from the viewpoint of the stability and the usability of the preparation.

The skin washing agent of the invention may have any form of solution, solubilizable form, emulsion, powdery dispersion, water/oil two-layer form, water/oil/powder three-layer form or the like.

EXAMPLES

The invention is described in more detail with reference to the following Examples; however, the invention should not be restricted at all by these Examples. Unless otherwise specifically indicated, the amount is in terms of % by weight based on the system in which the ingredient is incorporated. Because of easy use thereof, cosmetic materials are sold in a form of aqueous dilutions; however, the amount of the ingredient as referred to herein is all in terms of the content of the undiluted ingredient itself.

Prior to describing Examples, test methods and evaluation criteria employed for evaluation in Examples are described.
1. Preparation of Samples:

Samples (face washing agents) having the composition shown in Tables 1 to 3 below were used. The samples were produced as follows: Glycerin was added to ion-exchanged water, and various fatty acids were added thereto and dissolved under heat at 70° C. Potassium hydroxide solution was added thereto to neutralize it, thereby preparing a soap solution. Polymer and surfactant were added thereto and fully stirred. The solution was rapidly cooled to 25° C. to give a creamy face washing agent, and this preparation was tested.

In Tables 1 to 3, "DADMAC/acrylic acid copolymer" is DADMAC/acrylic acid of 50/50 (by mass) having a mass molecular weight of 4,500,000.

"DADMAC polymer" has a mass molecular weight of 250,000.

"DADMAC/acrylamide/acrylic acid copolymer" is DADMAC/acrylamide/acrylic acid of 25/50/25 (by mass) having a mass molecular weight of 4,000,000.

2. Evaluation Test Method and Evaluation:
[Foaming Speed in Washing]

The samples (face washing agents) shown in Tables 1 to 3 were tried by 10 expert panelists in a use test for the foaming speed in washing. The evaluation criteria are as mentioned below. The points given by the 10 panelists were averaged for the sample evaluation.
(Evaluation Criteria)
  5: Rapid foaming.
  4: Somewhat rapid foaming.
  3: Average
  2: Somewhat slow foaming.
  1: Slow foaming.

[Quality of Foams in Washing]
The samples (face washing agents) shown in Tables 1 to 3 were tried by 10 expert panelists in a use test for the quality of foams in washing. The evaluation criteria are as mentioned below. The points given by the 10 panelists were averaged for the sample evaluation.
(Evaluation Criteria)
  5: Creamy.
  4: Somewhat creamy.
  3: Average
  2: Somewhat non-creamy.
  1: Non-creamy.

[Skin Refreshed Feeling after Washing]
The samples (face washing agents) shown in Tables 1 to 3 were tried by 10 expert panelists in a use test for the skin refreshed feeling after washing. The evaluation criteria are as mentioned below. The points given by the 10 panelists were averaged for the sample evaluation.
(Evaluation Criteria)
  5: Refreshed feeling given.
  4: Somewhat refreshed feeling given.
  3: Average
  2: Refreshed feeling somewhat unsatisfactory.
  1: Refreshed feeling not given.

[Moist Skin Feeling after Washing]
The samples (face washing agents) shown in Tables 1 to 3 were tried by 10 expert panelists in a use test for the moist skin feeling after washing. The evaluation criteria are as mentioned below. The points given by the 10 panelists were averaged for the sample evaluation.
(Evaluation Criteria)
  5: Moist feeling given.
  4: Somewhat moist feeling given.
  3: Average
  2: Moist feeling somewhat unsatisfactory.
  1: Moist feeling not given.

[Absence of Skin Pulling Feeling after Washing]
The samples (face washing agents) shown in Tables 1 to 3 were tried by 10 expert panelists in a use test for the absence of skin pulling feeling after washing. The evaluation criteria are as mentioned below. The points given by the 10 panelists were averaged for the sample evaluation.
(Evaluation Criteria)
  5: No skin pulling feeling given.
  4: Skin pulling feeling not given in some degree.
  3: Average
  2: Skin pulling feeling given in some degree.
  1: Skin pulling feeling given.

[Change in Moisture Content of Skin after Washing]
Regarding the moisture content of skin after washed with any of the samples (face washing agents) shown in Tables 1 to 3, the moisture content of skin was measured respectively before washing and in 30 minutes after washing, and the sample was evaluated based on the skin moisture content change. The moisture content was measured with Corneometer CM825 (Courage+.Khazaka, Germany). The evaluation criteria are as mentioned below.
(Evaluation Criteria)
  ○: (skin moisture content after washing)−(skin moisture content before washing)≥0.
  x: (skin moisture content after washing)−(skin moisture content before washing)<0.

Examples 1 and 2, Comparative Examples 1 to 11

The samples shown in Table 1 below were tested and evaluated for the foaming speed, the quality of foams, the feeling after washing (refreshed feeling, moist feeling, no skin pulling feeling) and for the skin moisture content change, according to the above-mentioned evaluation methods. The results are shown in Table 1.

TABLE 1

| | Example | | Comparative Example | | | | | | | | | | |
|---|---|---|---|---|---|---|---|---|---|---|---|---|---|
| | 1 | 2 | 1 | 2 | 3 | 4 | 5 | 6 | 7 | 8 | 9 | 10 | 11 |
| Glycerin | 30 | 30 | 30 | 30 | 30 | 30 | 30 | 30 | 30 | 30 | 30 | 30 | 30 |
| Lauric Acid | 4 | 4 | 4 | 4 | 4 | 4 | 4 | 4 | 4 | — | 4 | 4 | 4 |
| Myristic Acid | 10 | 10 | 10 | 10 | 10 | 10 | 10 | 10 | 10 | — | 10 | 10 | 10 |
| Stearic Acid | 12 | 12 | 12 | 12 | 12 | 12 | 12 | 12 | 12 | — | 12 | 12 | 12 |
| Potassium Hydroxide | 4.8 | 4.8 | 4.8 | 4.8 | 4.8 | 4.8 | 4.8 | 4.8 | 4.8 | — | 4.8 | 4.8 | 4.8 |
| Polyglyceryl(4) Lauryl Ether | 3 | 3 | — | 3 | — | — | 3 | 3 | — | 3 | — | 3 | 3 |
| DADMAC/Acrylic Acid Copolymer | 0.3 | 0.3 | — | — | 0.3 | — | 0.3 | — | 0.3 | 0.3 | — | 0.3 | 0.3 |
| Acylmethyltaurine Sodium | 1.5 | — | — | — | — | 1.5 | — | 1.5 | 1.5 | 20 | — | — | — |
| Hydroxy Ether Sodium Carboxylate | — | 1.5 | — | — | — | — | — | — | — | — | — | — | — |
| Imidazolinium Betaine | — | — | — | — | — | — | — | — | — | — | 4 | 4 | — |
| Sodium Lauroylglutamate | — | — | — | — | — | — | — | — | — | — | — | — | 4 |
| Ion-Exchanged Water | bal. | bal. | bal. | bal | bal. | bal. | bal. | bal. | bal. | bal. | bal. | bal. | bal. |
| Foaming Speed | 4.8 | 5 | 2.8 | 2.6 | 2.6 | 3.6 | 2.8 | 3.6 | 3.6 | 3.2 | 2.6 | 2.8 | 2.8 |
| Quality of Foams in Washing (creaminess) | 5 | 4.8 | 2.4 | 2.6 | 2.6 | 2.4 | 3.2 | 2.8 | 3.2 | 2.6 | 3.6 | 3.2 | 3.2 |
| Refreshed Feeling after Washing | 4.8 | 4.8 | 4.8 | 4.8 | 4.8 | 4.6 | 4.6 | 4.2 | 4.2 | 1.8 | 4.2 | 4 | 4.2 |
| Moist Feeling after Washing | 4.8 | 4.8 | 1.8 | 2.2 | 2.8 | 3 | 2.8 | 3.8 | 2.8 | 3.4 | 3.2 | 2.8 | 3 |
| No Skin Pulling Feeling after Washing | 4.8 | 4.8 | 1.8 | 2.4 | 3 | 3 | 2.8 | 3.8 | 2.8 | 4.2 | 2.6 | 2.6 | 2.6 |
| Skin Moisture Content Change | ○ | ○ | x | x | x | x | x | x | x | ○ | x | x | x |

As shown in the results in Table 1, the face washing agent of Comparative Example 1 not containing the indispensable ingredients of the invention except component (a) was inferior in that, in washing, the foaming speed was low and the foams were not creamy; and after washing, the face washing agent could not give a skin moist feeling but gave a skin pulling feeling. On the other hand, the sample of Comparative Example 2 containing component (a) and component (c) and the sample of Comparative Example 3 containing component (a) and component (b) were improved in some degree in point of the foaming speed, the creaminess of foams, the moist feeling and the absence of skin pulling feeling; however, it could not be said that these effects would be sufficient.

As opposed to these, it has been clarified that the face washing agents of Examples 1 to 2 containing components (a) to (d) were significantly improved in point of the foaming speed and the creaminess of foams in washing and in point of the skin refreshed feeling, the moist feeling and the absence of skin pulling feeling after washing and that these face washing agents did not lower the skin moisture content.

However, as in Comparative Examples 5 to 8, these effects significantly reduced when anyone of component (a), component (b), component (c) and component (d) was not included in the compositions. As in Comparative Examples 9 and 10, where an ampholytic surfactant such as imidazolium betaine or a glutamate-type surfactant such as sodium lauroylglutamate was incorporated in the system that contains components (a) to (c), in place of component (d) therein, the compositions could not exhibit the effects of the invention.

Examples 3 to 13, Comparative Example 12

The samples shown in Table 2 below were tested and evaluated for the foaming speed, the quality of foams, the feeling after washing (refreshed feeling, moist feeling, no skin pulling feeling) and for the skin moisture content, according to the above-mentioned evaluation methods. The results are shown in Table 2.

TABLE 2

| | Example | | | | | | | | | | | Comp. Ex. |
|---|---|---|---|---|---|---|---|---|---|---|---|---|
| | 3 | 4 | 5 | 6 | 7 | 8 | 9 | 10 | 11 | 12 | 13 | 12 |
| Glycerin | 30 | 30 | 30 | 30 | 30 | 30 | 30 | 30 | 30 | 30 | 30 | 30 |
| Lauric Acid | 4 | 4 | 4 | 4 | 4 | 4 | 4 | 4 | 4 | 4 | 4 | 4 |
| Myristic Acid | 10 | 10 | 10 | 10 | 10 | 10 | 10 | 10 | 10 | 10 | 10 | 10 |
| Stearic Acid | 12 | 12 | 12 | 12 | 12 | 12 | 12 | 12 | 12 | 12 | 12 | 12 |
| Potassium Hydroxide | 4.8 | 4.8 | 4.8 | 4.8 | 4.8 | 4.8 | 4.8 | 4.8 | 4.8 | 4.8 | 4.8 | 4.8 |
| Polyglyceryl(4) Lauryl Ether | 3 | — | — | — | — | — | — | — | — | 3 | 3 | — |
| Polyglyceryl(4) Stearyl Ether | — | 3 | — | — | — | — | — | — | — | — | — | — |
| Polyglyceryl(4) Arachyl Ether | — | — | 3 | — | — | — | — | — | — | — | — | — |
| Polyglyceryl(4) Octyl Ether | — | — | — | 3 | — | — | — | — | — | — | — | — |
| Polyglyceryl(6) Hexyl Ether | — | — | — | — | 3 | — | — | — | — | — | — | — |
| Polyglyceryl(3) Lauryl Ether | — | — | — | — | — | 3 | — | — | — | — | — | — |
| Polyglyceryl(10) Lauryl Ether | — | — | — | — | — | — | 3 | — | — | — | — | — |
| Polyglyceryl(20) Lauryl Ether | — | — | — | — | — | — | — | 3 | — | — | — | — |
| Polyglyceryl(25) Lauryl Ether | — | — | — | — | — | — | — | — | 3 | — | — | — |
| Polyglyceryl(2) Lauryl Ether | — | — | — | — | — | — | — | — | — | — | — | 3 |
| DADMAC/Acrylic Acid Copolymer | 0.3 | 0.3 | 0.3 | 0.3 | 0.3 | 0.3 | 0.3 | 0.3 | 0.3 | — | — | 0.3 |
| DADMAC Polymer | — | — | — | — | — | — | — | — | — | 0.3 | — | — |
| DADMAC/Acrylamide/Acrylic Acid | — | — | — | — | — | — | — | — | — | — | 0.3 | — |

TABLE 2-continued

|  | Example |  |  |  |  |  |  |  |  |  |  | Comp. Ex. |
|---|---|---|---|---|---|---|---|---|---|---|---|---|
|  | 3 | 4 | 5 | 6 | 7 | 8 | 9 | 10 | 11 | 12 | 13 | 12 |
| Copolymer |  |  |  |  |  |  |  |  |  |  |  |  |
| Acylmethyltaurine Sodium | 1.5 | 1.5 | 1.5 | 1.5 | 1.5 | 1.5 | 1.5 | 1.5 | 1.5 | 1.5 | 1.5 | 1.5 |
| Ion-Exchanged Water | bal. | bal. | bal. | bal. | bal. | bal. | bal. | bal. | bal. | bal. | bal. | bal. |
| Foaming Speed | 4.8 | 4.6 | 4.4 | 4.8 | 4.8 | 4.4 | 4.8 | 4.8 | 4.8 | 4.8 | 4.8 | 3.6 |
| Quality of Foams in Washing (creaminess) | 5 | 5 | 5 | 5 | 4.4 | 4.6 | 5 | 5 | 5 | 5 | 5 | 3.6 |
| Refreshed Feeling after Washing | 4.8 | 4.8 | 4.8 | 4.8 | 4.8 | 4.6 | 4.8 | 4.8 | 4.8 | 4.8 | 4.8 | 4.2 |
| Moist Feeling after Washing | 4.8 | 4.6 | 4.6 | 4.8 | 4.8 | 4.6 | 4.8 | 4.8 | 4.8 | 4.6 | 4.6 | 3.8 |
| No Skin Pulling Feeling after Washing | 4.8 | 4.8 | 4.8 | 4.8 | 4.6 | 4.6 | 4.8 | 4.6 | 4.2 | 4.6 | 4.6 | 3.8 |
| Skin Moisture Content Change | ○ | ○ | ○ | ○ | ○ | ○ | ○ | ○ | ○ | ○ | ○ | x |

As shown in the results in Table 2, the samples in which the alkyl group in component (c) is from hexyl having 6 carbon atoms to arachyl having 20 carbon atoms exhibited excellent effects of improvement. Above all, it has been confirmed that the samples in which the group has at least 8 more carbon atoms exhibited a noticeably excellent effect of improving the creaminess of foams that and the samples in which the group has at most 16 carbon atoms exhibited a noticeably excellent effect of improving the foaming speed.

The degree of polymerization of polyglycerin in component (c) was varied from 2 to 25. As in Comparative Example 12, the sample could not exhibit the effects of the invention when the degree of polymerization was 2; and it has been confirmed that the effects of the invention could be attained only when the degree of polymerization is at least 3.

Examples 14 to 21

The samples shown in Table 3 below were tested and evaluated for the foaming speed, the quality of foams, the feeling after washing (refreshed feeling, moist feeling, no skin pulling feeling) and for the skin moisture content, according to the above-mentioned evaluation methods. The results are shown in Table 3.

TABLE 3

|  | Example |  |  |  |  |  |  |  |
|---|---|---|---|---|---|---|---|---|
|  | 14 | 15 | 16 | 17 | 18 | 19 | 20 | 21 |
| Glycerin | 30 | 30 | 30 | 30 | 30 | 30 | 30 | 30 |
| Lauric Acid | 4 | 4 | 4 | 4 | 4 | 4 | 4 | 4 |
| Myristic Acid | 10 | 10 | 10 | 10 | 10 | 10 | 10 | 10 |
| Stearic Acid | 12 | 12 | 12 | 12 | 12 | 12 | 12 | 12 |
| Potassium Hydroxide | 4.8 | 4.8 | 4.8 | 4.8 | 4.8 | 4.8 | 4.8 | 4.8 |
| Polyglyceryl(4) Lauryl Ether | 0.05 | 0.1 | 2 | 5 | 3 | 3 | 3 | 3 |
| DADMAC/Acrylic Acid Copolymer | 0.3 | 0.3 | 0.3 | 0.3 | 0.05 | 1 | 5 | 10 |
| Acylmethyltaurine Sodium | 1.5 | 1.5 | 1.5 | 1.5 | 1.5 | 1.5 | 1.5 | 1.5 |
| Ion-Exchanged Water | bal. | bal. | bal. | bal. | bal. | bal. | bal. | bal. |
| Foaming Speed | 4.2 | 4.6 | 4.8 | 4.8 | 4.8 | 4.6 | 4.4 | 4 |
| Quality of Foams in Washing (creaminess) | 4.4 | 5 | 5 | 5 | 4.4 | 5 | 5 | 5 |
| Refreshed Feeling after Washing | 4.2 | 4.8 | 4.8 | 4.8 | 4.8 | 4.8 | 4.8 | 4.8 |
| Moist Feeling after Washing | 4.2 | 4.6 | 4.6 | 4.8 | 4.8 | 4.8 | 4.8 | 4.8 |
| No Skin Pulling Feeling after Washing | 4.4 | 4.8 | 4.8 | 4.8 | 4.6 | 4.8 | 4.6 | 4.6 |
| Skin Moisture Content Change | ○ | ○ | ○ | ○ | ○ | ○ | ○ | ○ |

Formulation Examples are shown below.

Example 22

Face Washing Agent

| (Constituents) | (% by mass) |
|---|---|
| (1) Glycerin | 15.0 |
| (2) Polyethylene Glycol 400 | 5.0 |
| (3) Lauric Acid | 5.0 |
| (4) Myristic Acid | 10.0 |
| (5) Palmitic Acid | 10.0 |
| (6) Stearic Acid | 15.0 |
| (7) Lauroylmethyltaurine Sodium | 5.0 |
| (8) Fatty Acid Monoglyceride | 1.0 |
| (9) Polyglyceryl(4) Lauryl Ether | 2.0 |
| (10) DADMAC/Acrylamide Copolymer | 1.0 |
| (11) Potassium Hydroxide | 6.0 |
| (12) Ion-Exchanged Water | bal. |
| (13) Chelating Agent | q.s. |
| (14) Fragrance | q.s. |

(Production Method)

(1) to (8) were added to (12), heated at 75° C., and dissolved. After dissolution, this was neutralized with (11), and subsequently, (10) and (9), (13) and (14) were added thereto and fully stirred, and thereafter cooled to give the present product.

The face washing agent of Example 22 was excellent in the foaming speed and the creaminess of foams in washing, and in the refreshed feeling, the moist feeling and the absence of skin pulling feeling after washing, and, gave no skin moisture content change before and after washing.

Example 23

Body Shampoo

| (Constituents) | (% by mass) |
|---|---|
| (1) Glycerin | 15.0 |
| (2) Polyethylene Glycol 1500 | 5.0 |
| (3) Lauric Acid | 2.0 |
| (4) Myristic Acid | 5.0 |
| (5) Palmitic Acid | 5.0 |
| (6) Stearic Acid | 7.0 |
| (7) Lauroylmethyltaurine Sodium | 5.0 |
| (8) Lauryl Glycol Sodium Acetate | 1.0 |
| (9) Potassium Hydroxide | 3.0 |
| (10) Polyglyceryl(10) Lauryl Ether | 3.0 |
| (11) DADMAC Polymer | 1.0 |
| (12) Ion-Exchanged Water | bal. |
| (13) Fragrance | q.s. |

(Production Method)

(1) to (6) were added to (12), heated at 75° C., and dissolved. After dissolution, this was neutralized with (9), and subsequently, (11) and (7), (8), (10) and (13) were added thereto and fully stirred, and thereafter cooled to give the present product.

The body shampoo of Example 23 was excellent in the foaming speed and the creaminess of foams in washing, and in the refreshed feeling, the moist feeling and the absence of skin pulling feeling after washing, and gave no skin moisture content change before and after washing.

Industrial Applicability

The foamable skin washing agent of the invention has the advantages of detergency, rapid foamability in washing, excellent creaminess of foams, impartation of no skin pulling feeling after washing, impartation of moist feeling to skin and no influence of reducing the skin moisture content, which are remarkably more excellent than those of conventional washing agents.

The invention claimed is:

1. A foamable skin washing agent comprising (a) a fatty acid salt having from 10 to 22 carbon atoms, (b) one or more polymers selected from a homopolymer, a dipolymer and a terpolymer derived from a cationated monomer represented by the following formula (I):

$$H_2C=HC-CH_2\underset{\underset{R_2}{\overset{R_1}{N^+}}}{}CH_2-CH=CH_2 \quad Y^- \quad (I)$$

(in formula (I), $R_1$ and $R_2$ each independently represent a hydrogen atom, or an alkyl group having from 1 to 4 carbon atoms; and $Y^-$ represents a monovalent inorganic or organic anion), wherein in the dipolymer or in the terpolymer the cationated monomer is copolymerizable with one of more selected from the group consisting of a nonionic monomer, anionic monomer and an ampholytic monomer, wherein the nonionic monomer is one or more selected from the group consisting of acrylamide, methacrylamide, N-methacrylamide, N-methylmethylacrylamide, N,N-dimethylacrylamide, N,N-diethylmethacrylamide, N-cyclohexylacrylamide, N-cyclohexylmathacrylamide, N,N-di(ethylene glycoil) acrylamide, N,N-di(ethylene glycol) methacrylamide, N,N-polyethylene glycol acrylamide, N-polyethylehe glycol methacrylamide, N-polyethylene glycol ethyl ether acrylamide, and N-polyethylene glycol ethyl ether methacrylamide monomers, wherein the anionic monomer is at least one selected from the group consisting of acrylic acid, methacrylic acid, sodium acrylate, sodium methacrylate, ammonium acrylate, and ammonium methacrylate, and wherein the ampholytic monomer is at least one of N-aminopropylacrylamide-betaine and N-aminopropylmethacrylamide-betaine, (c) a polyglyceryl monoalkyl ether represented by the following formula (II):

$$C_nH_{2n+1}-O-\left[CH_2-\underset{OH}{CH}-CH_2-O\right]_m H \quad (II)$$

(in the formula (II), n indicates an integer of from 6 to 22, and m indicates an integer of 3 or more), (d) one or more selected from an acylmethyltaurine salt which is represented by the following formula (III)

$$R_3-CON\underset{R_4}{}CCH_2CH_2-SO_3M_1, \quad (III)$$

wherein in formula (III), $R^3$ represents an alkyl group or an alkenyl group having from 7 to 21 carbon atoms; and $R^4$ represents an alkyl group having from 1 to 3 carbon atoms, and a hydroxyalkyl ether carboxylate salt.

2. The foamable skin washing agent as claimed in claim 1, wherein component (b) is one or more polymers selected from dimethyldiallylammonium chloride polymers, dimethyldiallylammonium chloride/acrylamide copolymers, and dimethyldiallylammonium chloride/acrylamide/acrylic acid copolymers.

3. The foamable skin washing agent as claimed in claim 1, which contains component (a) in an amount of from 2 to 90% by mass, component (b) in an amount of from 0.01 to 10% by mass, component (c) in an amount of from 0.01 to 20% by mass, and component (d) in an amount of from 1 to 20% by mass.

4. A foamable skin washing agent of claim 1, wherein the fatty acid salt has from 10 to 20 carbon atoms.

* * * * *